United States Patent [19]

Hanson et al.

[11] 4,251,509

[45] Feb. 17, 1981

[54] DRY PARTICULATE VACCINE FOR ORAL ADMINISTRATION

[75] Inventors: Robert P. Hanson, Madison, Wis.; Adedipe Abegunde, Usi-Ekiti, Nigeria

[73] Assignee: Wisconsin Alumni Research Foundation, Madison, Wis.

[21] Appl. No.: 117,253

[22] Filed: Jan. 31, 1980

Related U.S. Application Data

[63] Continuation of Ser. No. 943,209, Sep. 18, 1978, abandoned.

[51] Int. Cl.$^3$ .................................... A61K 39/17
[52] U.S. Cl. ..................................... 424/89; 424/35;
424/36; 424/93
[58] Field of Search .................. 424/35, 36, 89, 93

[56] References Cited

U.S. PATENT DOCUMENTS

| | | | |
|---|---|---|---|
| 2,744,015 | 5/1956 | Katsube | 424/93 |
| 2,809,112 | 10/1957 | Anderson et al. | 424/93 |
| 3,072,528 | 1/1963 | Kludas et al. | 424/93 |
| 3,285,748 | 11/1966 | Koonz et al. | 424/93 |
| 3,823,228 | 7/1974 | Ferris et al. | 424/93 |
| 3,956,482 | 5/1976 | Hahn et al. | 424/93 |
| 3,957,974 | 5/1976 | Hata | 424/93 |

*Primary Examiner*—Shep K. Rose
*Attorney, Agent, or Firm*—McDougall, Hersh & Scott

[57] ABSTRACT

A vaccine in the form of a dry particulate comprising a matrix formed of a protein component as a binder and sugar as a solubilizing agent and which includes an antigen in the matrix in an amount to provide for a titre in excess of $1 \times 10^5$ units per particulate and in which the moisture content is less than 1.0% by weight and which may include an antioxidant to stabilize the vaccine, an immunostimulant to enhance the response of the vaccine and a facilitator to enhance cell entry.

14 Claims, No Drawings

DRY PARTICULATE VACCINE FOR ORAL ADMINISTRATION

This is a continuation of application Ser. No. 943,209, filed Sept. 18, 1978, now abandoned.

This invention relates to a vaccine and to a method for preparation of same.

The invention will be described with reference to a vaccine for use in the protection of chickens against Newcastle disease, but it will be understood that the concepts of the invention will have application also to the use of other virus in vaccines to combat diseases other than Newcastle disease and for use with animals such as turkeys, cows, pigs, sheep and the like other than chickens. However, description of the general concepts as applied to chickens and Newcastle disease will greatly simplify the description of the invention to be described and claimed herein.

Vaccines have been developed for administration to chickens en masse i.e. applied by air spray or in drinking water. These techniques of administration are now being extensively used throughout the world and have stimulated the development of similar vaccines for use with many other animals.

Administration of the vaccine by inclusion in the drinking water is limited in use by the fact that the vaccines are often fragile in water and last for only a very short time. As a result, an animal to be vaccinated must be made to drink soon after the vaccine strain is introduced into the water. This limits such mass administration to chickens or other animals that are domesticated or under control, such as being maintained within a confined or concentrated area. Such mass administration would not be suitable for use in immunizing stray animals in the field.

Similarly, administration of the vaccine by spraying into the environment is applicable to areas where the chickens or other animals can be confined and not to chickens or other animals in the open field.

The problem of vaccination of chickens in the open field is especially acute in less developed nations where reliance may be had on a poultry population that can be rapidly developed as a source of food. In times after feed grain stocks are depleted, i.e., after a famine, when grain supplies again become abundant, grain storage is a problem and a need exists for utilizing the excess grain. A rapid developing poultry population can convert excess grain into both a source of food and income. The development of other slower populating sources, such as cattle, sheep, and pigs, and the like for meat takes a relatively much longer time.

Much of the poultry population in less developed nations in not confined and must scavenge for part of its food. If these birds becme infected with Newcastle disease it spreads to confined chickens. Thus, particularly in such underdeveloped countries, it is desirable to be able to provide for vaccination of such scavenger birds, as well as confined chickens, to protect poultry against Newcastle disease.

It is an object of this invention to provide a method and composition which is effective and which is practical for use in the treatment of chickens and other animals while at stray in the field or domestically raised in a confined area for vaccination of the same against various killing diseases such as Newcastle disease, which can be administered without any special training thereby to enable effective utilization in the underdeveloped countries of the world; which can be employed without fear that the antigen will become ineffective by dilution or by inactivation during the process of administration; in which the composition used for administration of the antigen can be formulated to include additives which preserve the activity of the antigen, stimulate the immune response, and facilitate the penetration of the antigen into the target for accelerating the response; and in which the antigen can be formulated for most effective and safe use and in amounts to achieve the desired response without endangering the human species or environment.

These and other objects and advantages will hereinafter appear from the following description which is given by way of illustration and not by way of limitation of the invention.

Briefly described, in accordance with the practice of this invention, the antigen or virus of the vaccine is incorporated in an effective amount in a dry particulate for administration as an oral vaccine in a stabilized form which may be made available for ingestion by stray chickens and other animals in the field, and in a form acceptable to such stray field animals as well as domesticated birds and animals in a confined or concentrated area. By making the vaccine available in a solid particulate for oral administration, the desired amount of antigen can be incorporated into the particulate feed in a composition which may contain stabilizing agents, stimulating agents, as well as facilitators to increase the penetration of the cells by the antigen or virus thereby to enchance the response to the vaccine. Ingestion of the solid particulate containing the vaccine is effective to induce immunity in free ranging animals.

The strains of vaccine capable of use in the preparation of a solid particulate vaccine embodying the features of this invention are (1) a vaccine having the ability to induce immunity to virulent strains of the homologous virus as characterized by 90% survival of vaccinates from a challenge that kills 90% of the susceptibles, (2) innocuity characterized by the inability to produce clinical disease in a recipient of any age even when receiving ten times the recommended dosage, (3) high thermostability as characterized by retention of high infectious titre after 30 days at a temperature of 37° C., and (4) infects by the gastrointestinal route and stimulates a good response by serological tests or by challenge as described above, and by the inability to produce plaques without the addition of magnesium.

An example of a suitable vaccine strain is Newcastle disease vaccine, sometimes referred to as V-4 strain. It provides immunity to Newcastle disease, it is thermostable and is resistant to environmental deterioration such that it can stand up in the open field for use with stray animals.

The most desirable form in which the vaccine is made available as a virus for ingestion by stray chickens and other animals is in a dry particulate form, such as pellets. The virus made available in the form of pellets will be devoured by chickens or other animals that eat grain or other particulate feed. However, the virus can be made available for ingestion in other dry particulate forms.

The practice of this invention will be illustrated by the following examples.

EXAMPLE 1

Propagation of Virus

The virus can be propagated by techniques well known to the art in a suitable host system. In the case of Newcastle disease virus, such as V-4 strain, the host can comprise chicken egg embryo which is inoculated with the virus strain through the shell and harvested by opening the egg to remove the allantoic fluid having a titre of about $1 \times 10^9$. The titre being a measurement of the biological activity of the virus.

EXAMPLE 2

Concentration of Virus

The virus is concentrated before formulation in a pelletized vaccine by incorporation with mixing into an equeous solution of 0.8% by weight dextran and 5.8% by weight polyethylene glycol to enable its separation as a concentrate. By such concentration, the number of infective units is increased more than one hundred fold.

Instead of concentrating the virus by the precipitation method described above, the virus can be concentrated by evaporation of the fluid with which it is removed from the host egg.

EXAMPLE 3

Preparation of Pelletized Vaccine

A suitable solid matrix for the virus strain should contain both an adhesive, such as a protein, and a solubilizing agent, such as a sugar. Casein is representative of a suitable protein since it stabilizes the virus, provides the bulk carrier for the virus and it has the adhesive properties desired for forming the desired particulate. Lactose is representative of a suitable sugar since it facilitates solubilization on the ingestion of the pellets in the vaccinates. The casein or other protein can be used alone or as a part of the non-fat milk solid. Use can also be made of serum solids, but milk solids, with or without additional casein or other proteins, are preferred because of the lesser expense. The ratio of materials used in formulating the matrix is not significant.

The virus is admixed with the matrix materials is an amount so that the dried pellets will have a titre of at least $1 \times 10^5$ and preferably more than $1 \times 10^7$. Pellets having a titre of less than $1 \times 10^5$ will offer little, if any, protection, while anything more than $1 \times 10^7$ will not be harmful. A titre within the range of $1 \times 10^7$ to $1 \times 10^9$ is most desirable for strong immunity.

The mixture of matrix materials and virus is formed into a paste by the admixture with additional water if necessary. The paste is extruded into a ribbon which can be subdivided into pellets of the desired titre and then dried in cold dry air to a moisture content of less than 0.5% by weight and preferably to about 0.25% by weight or less. When the amount of moisture exceeds 1.0% by weight, the virus is subject to decreased stability. It is desirable to maintain the material at ambient temperature or less during the prepartion of the pellets.

Thereafter, the dried pellets can be packaged under vacuum or in an inert atmosphere ($N_2$) in a pouch of plastic material or other container which is highly impervious to oxygen or water vapor such as in a package formed of polyethylene, polyamide resin or an ionic polyethylene-carboxylic acid polymer of the type marketed by E.I. Dupont under the trade name Surlyn. The packaged vaccine remains stable over an extended period of time to enable storage or shipment to distant stations for use.

The pellets or dry particulate vaccine can also be formed of a dry powder mixture, instead of a paste, if use is made of a cold press for pelletizing. It is preferred, however, to work with a paste since less heat is involved and dusting can be avoided.

The pellets can be distributed over the ground where the stray chickens feed or roam or the pellets can be incorporated with the grains for chickens or other animals.

Immunity to Newcastle disease will result from the ingestion of one or more pellets by the chickens or other animals. For achieving the desired immunization, it is desirable to revaccinate by distributing the pellets as feed on about six month intervals and preferably about three times a year.

The stability of the vaccine can be increased by the inclusion of an antioxidant as a component of the pellet or dry particulate vaccine. Dithiothreitol is representative of an antioxidant suitable for use to prolong the viability of the virus and to increase the period of thermostability to at least 30 days at 37° C. to maintain a titre sufficient to provide immunity. Other antioxidants can be used, the selection of which will depend on the particular virus which can be determined by sample tests well known to the trade. For this purpose, the antioxidant can be incorporated into the system in an amount within the range of 0.01% to 0.03% formula weight.

The response of the vaccinate to the virus can be stimulated by the inclusion of an immunostimulant such as levamisole in the vaccine. This enhances the response in stressed animals when the antigenic dose is minimal. Such immunostimulant can be employed in the vaccine in an amount within the range of 0.5% to 0.7% formula weight.

Penetration of the virus into the cells of the animal to increase responsiveness can be enhanced by the inclusion into the vaccine of a cell entry facilitator, such as magnesium sulphate. For this purpose, the cell entry facilitator can be incorporated in an amount up to and preferably in an amount within the range of 0.3% to 3% formula weight.

It will be understood that such additives are not essential to the feasibility of the dry particulate vaccine to provide the desired immunity. However, when used, they should be incorporated by admixture into the matrix before converting to the particulate form.

It will be understood that the concepts of this invention will have application to the preparation of a dry particulate vaccine containing virus strains other than Newcastle disease virus for use as an oral vaccine for immunizing against other animal diseases.

The following are specific examples of compositions of dry particulate vaccines representative of the practice of this invention.

EXAMPLE 4

|  | % by Weight |
| --- | --- |
| Dry milk solids | 4.0 gm - 62% |
| Lactose | 1.0 gm - 15% |
| Newcastle virus strain allantoic fluid | 1.5 gm. - 23% |
|  | 6.5 gm - 100% |

EXAMPLE 5

The composition is the same as in example 4, but includes dithiothreitol in the amount of 13 mg.

EXAMPLE 6

The composition is the same as that in example 4 except that it includes levamisole in the amount of 38 mg.

EXAMPLE 7

The composition is the same as that in example 4 except that it includes magnesium sulphate in the amount of 20 mg.

EXAMPLE 8

The composition is the same as that in example 4 except that it includes dithiothreitol in the amount of 13 mg., levamisole in the amount of 38 mg and magnesium sulphate in the amount of 20 mg.

The pellets or other dry particulate are prepared as described in example 3.

It will be understood that changes may be made in the details of formulation and operation without departing from the spirit of the invention, especially as defined in the following claims.

I claim:

1. An oral vaccine for poultry and animals in the field comprising as the essential ingredients, protein as a binder, sugar as a solubilizing agent and an antigen in an amount to provide a titre of at least $1\times10^5$ units per particulate, in which the antigen is characterized as a vaccine having the ability to induce immunity to virulent strains of the homologeous virus, inocuity characterized by the inability to produce clinical disease in a recipient taking 10 times the recommended dosage, high thermostability characterized by infectious titre after 30 days at a temperature of 37° C., which infects by gastrointestinal route, and stimulates good response by seriological tests, said particulate having a moisture content of less than 1% by weight, and as non-essential ingredients an antioxidant up to 0.03% by weight to stabilize the vaccine, an immunostimulant up to 0.7% by weight to enhance response to the vaccine and a facilitator up to 3% by weight to enhance entry of the vaccine.

2. A vaccine as claimed in claim 1 in which the antioxidant is dithiothretal present in an amount within the range of 0.01-0.03% by weight.

3. A vaccine as claimed in claim 1 in which the immunostimulant is Levamisole present in an amount within the range of 0.05-0.07% by weight.

4. A vaccine as claimed in claim 1 in which the facilitator is magnesium sulphate present in an amount within the range of 0.3-3% by weight.

5. The method for vaccines for poultry and animals in the field comprising distributing the particulate vaccine of claim 1 in the field in which said poultry and animals roam.

6. A vaccine as claimed in claim 1 in which the moisture content is less than 0.5% by weight of the particulate.

7. A vaccine as claimed in claim 1 in which the dry particulate is in the form of pellets of grain size.

8. A vaccine as claimed in claim 1 in which the binder component comprises a casein.

9. A vaccine as claimed in claim 1 in which the binder component is a non-fat milk solid which may include additional casein.

10. A vaccine as claimed in claim 1 in which the sugar is lactose.

11. A vaccine as claimed in claim 1 in which the antigen is a thermostable Newcastle disease virus for immunization of chickens.

12. A vaccine as claimed in claim 1 in which the facilitator is magnesium sulphate.

13. A method for preparing the dry particulate vaccine of claim 1 comprising mixing the matrix forming components with the antigen to form a paste, extruding the paste and subdividing the extrudant into pellets, and drying the pellets to a moisture content of less than 0.5% by weight.

14. The method as claimed in claim 13 in which the steps are carried out with the materials at a temperature of room temperature or below.

* * * * *